United States Patent [19]

Iida et al.

[11] Patent Number: 5,627,290
[45] Date of Patent: May 6, 1997

[54] 2,3-DIDEHYDROSIALIC ACID SUBSTITUTED WITH FLUORINE AT 7-POSITION AND SYNTHETIC INTERMEDIATE THEREOF

[75] Inventors: Takao Iida; Yutaka Ohira, both of Ibaraki, Japan

[73] Assignee: Daikin Industries, Ltd., Osaka, Japan

[21] Appl. No.: 586,908

[22] PCT Filed: Apr. 26, 1995

[86] PCT No.: PCT/JP95/00820

§ 371 Date: Jan. 26, 1996

§ 102(e) Date: Jan. 26, 1996

[87] PCT Pub. No.: WO95/32955

PCT Pub. Date: Dec. 7, 1995

[30] Foreign Application Priority Data

May 27, 1994 [JP] Japan ................................. 6-115014

[51] Int. Cl.$^6$ ................. C07D 309/14; C07D 309/28; C07H 5/06; C07H 5/10
[52] U.S. Cl. ..................... 549/419; 549/417; 536/17.2
[58] Field of Search .................... 549/417, 419; 536/17.2

Primary Examiner—Johann Richter
Assistant Examiner—Laura L. Stockton
Attorney, Agent, or Firm—Birch, Stewart, Kolasch & Birch, LLP

[57] ABSTRACT

The invention pertains to 2,7-Deoxy-7-fluoro-2,3-didehydrosialic acid and an intermediate thereof which are useful for developing practical drugs, such as an antiviral agent, a preventing agent for viral diseases, etc. and for a clinical application. In addition, they are also useful as a carcinostatic agent and an immunomodulation agent.

11 Claims, No Drawings

2,3-DIDEHYDROSIALIC ACID SUBSTITUTED WITH FLUORINE AT 7-POSITION AND SYNTHETIC INTERMEDIATE THEREOF

This application is a 371 of PCT JP95/00820 filed Apr. 26, 1995.

TECHNICAL FIELD

The present invention relates to 2,7-dideoxy-7-fluoro-2, 3-didehydrosialic acid, and a synthetic intermediate thereof.

RELATED ART

Sialic acid (a1) exists at the terminal end of glycoproteins and glycolipids in a living body, particularly an interior of animals, and plays an important role for a life sustainment, such as an adhesion between cells, a transmission of information, a delivery of hormone, etc. In order to elucidate the functions of sialic acid on the molecular level, various derivatives of sialic acid have been synthesized by chemical modifications.

Regarding derivatives of 2,3-didehydrosialic acid, a natural type (a2) [Haruo OGURA, Chem. Pharm. Bull., 36, 1872–1876 (1988)], 4-amino (a3) and 4-guanidino (a4) derivatives [M. von Itzstein et al., Carbohydr. Res., 259, 301–305 (1994)] have been synthesized, and their antiviral actions on influenza virus have been known. Regarding fluorine-containing derivatives of sialic acid, a 2-F derivative (a5) [(M. N. Sharma et al., Carbohydr. Res., 127, 201–210 (1984)], a 3-F derivative (a6) [Tatsuo IDO et al., Agric. Biol. Chem., 52, 1209–1215 (1988)] and a 9-F derivative (a7) [W. Korytnyk et al., J. Carbohydr. Chem., 1, 311–315 (1982–1983)] have been synthesized. Among them, the 3-F derivative exhibits a sialidase inhibition action and the 9-F derivative exhibits a carcinostatic action.

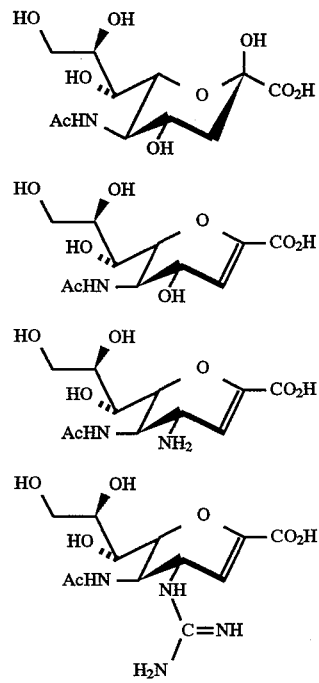

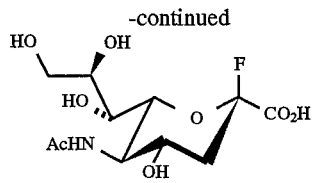

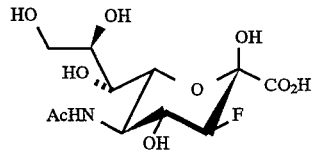

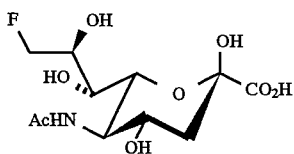

As described above, the didehydro derivatives and fluorine-containing derivatives of sialic acid have various physiological activities.

It is expected to enhance physiological activities and impart a selectivity by combining properties of didehydro derivatives with those of fluorine-containing sialic acid.

In the synthesis method of sialic acid, a large amount of sialic acid can be obtained from N-acetyl-D-mannosamine and pyruvic acid by using an enzyme method. Accordingly, the 7-position of sialic acid corresponds to the 4-position of N-acetyl-D-mannosamine. In order to introduce a fluorine atom at the 4-position of N-acetyl-D-mannosamine while maintaining the configuration, N-acetyl-D-talosamine is required. N-acetyltalosamine exits in the cartilage of the trachea of sheep, but is scarce. N-acetyltalosamine can be produced by the synthesis from lyxose (R. Kuhn et al., Ann, 1958, 612, 65) and by the epimerization of the 3-position of D-idosamine derivatives (R. W. Jeanioz et al., J. Org. Chem., 1961, 26, 532). However, these methods are not suitable because, for example, the synthetic process has many steps.

SUMMARY OF THE INVENTION

An object of the present invention is to provide 2,7-dideoxy-7-fluoro-2,3-didehydrosialic acid which is expected as drugs such as antiviral agents, carcinostatic agents, immunomodulation agents, etc., and synthetic intermediates thereof.

The present inventors have researched for the purpose of synthesizing an analogue obtained by chemically modifying a side chain moiety of sialic acid with fluorine, and succeeded in synthesizing the analogue. Thus, the present invention has been accomplished.

In the present invention, N-acetyl-D-galactosamine is available in the same degree of ease as that in case of N-acetyl-D-mannosamine. Therefore, 2,7-dideoxy-7-fluoro-2,3-didehydrosialic acid can be easily synthesized by using N-acetyl-D-galactosamine as the starting raw material. Namely, 2,7-dideoxy-7-fluoro-2,3-didehydrosialic acid can be synthesized by protecting hydroxyl groups other than the hydroxyl group at the 4-position of N-acetyl-D-galactosamine, subjecting the hydroxyl group at the 4-position to Walden inversion simultaneously with introducing a fluorine atom, to give N-acetyl-4-deoxy-4-fluoro-D-glucosamine, isomerizing and subjecting it to aldol reaction together with pyruvic acid through the use of an enzyme (N-acetylneuraminic acid aldolase) to construct a novel route for synthesizing the objective 7-deoxy-7-fluoro-sialic acid, and then forming an intermediate from the resulting 7-fluorosialic acid to give 2,7-dideoxy-7-fluoro-2,3-didehydrosialic acid.

The present invention provides a compound represented by the formula (I):

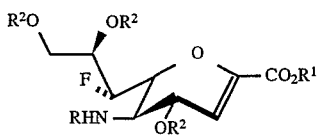

wherein R is an aliphatic acyl group; $R^1$ is a hydrogen atom or a lower alkyl group; and $R^2$ is a hydrogen atom, or an aliphatic or aromatic acyl group; provided that $R^2$ indicates a hydrogen atom when $R^1$ is a hydrogen atom and $R^2$ indicates an aliphatic or aromatic acyl group when $R^1$ is a lower alkyl group (each $R^2$ may be the same or different).

The present invention provides a compound represented by the formula (II):

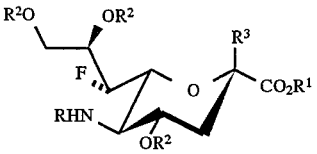

wherein R is an aliphatic acyl group; $R^1$ is a lower alkyl group; $R^2$ is an aliphatic or aromatic acyl group (each $R^2$ may be the same or different); and $R^3$ is a halogen atom.

The present invention provides a compound represented by the formula (III):

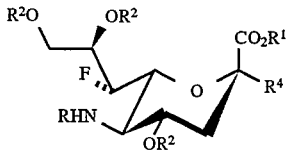

wherein R is an aliphatic acyl group; $R^1$ is a lower alkyl group; $R^2$ is a hydrogen atom, or an aliphatic or aromatic acyl group (each $R^2$ may be the same or different); and $R^4$ is a thioacyl group, a thioalkyl group or a thioaryl group; provided that $R^2$ indicates an aliphatic or aromatic acyl group, when $R^4$ is a thioacyl group, a thioalkyl group or a thioaryl group (each $R^2$ may be the same or different).

The present invention provides a 2,3-didehydrosialic acid derivative represented by the formula (IV):

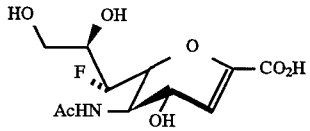

wherein Ac is an acetyl group.

The present invention provides a N-acetyl-7-deoxy-7-fluoro-neuraminic acid derivative represented by the formula (X):

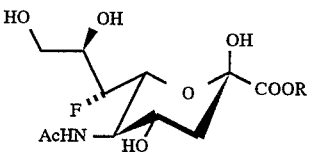

wherein R is hydrogen or an alkyl group having 1 to 20 carbon atoms (preferably 1 to 4 carbon atoms); and Ac is an acetyl group.

The present invention provides 1,3-di-O-acetyl-2-acetamido-2,4-dideoxy-4-fluoro-6-O-trityl-α-D-glucopyranose represented by the formula:

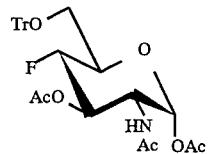

wherein Tr is $(C_6H_5)_3O$—.

The present invention provides 4-deoxy-4-fluoro-D-glucosamine hydrochloride represented by the formula:

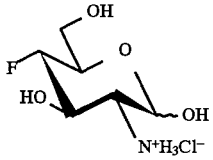

In addition, the present invention provides a process for producing N-acetyl-7-deoxy-7-fluoro-neuraminic acid, which comprises subjecting N-acetyl-4-deoxy-4-fluoro-D-glucosamine and sodium pyruvate to a condensation reaction with N-acetyl-neuraminic acid aldolase.

Further, the present invention provides a process for producing N-acetyl-7-deoxy-7-fluoro-neuraminic acid alkyl ester, which comprises esterifying N-acetyl-7-deoxy-fluoro-neuraminic acid by the reaction with an alcohol having a $C_1$–$C_{20}$ alkyl group.

Furthermore, the present invention provides a process for producing N-acetyl-4-deoxy-4-fluoro-D-glucosamine, which comprises subjecting 1,3-di-O-acetyl-N-acetyl-D-galactosamine to tritylation, fluorination, detritylation and hydrolysis with hydrochloric acid, and then subjecting the resulting 4-deoxy-4-fluoro-D-glucosamine hydrochloride to N-acetylation.

DETAILED EXPLANATION OF THE INVENTION

In the compounds (I), (II), (III) and (IV), R, $R^1$, $R^2$, $R^3$ and $R^4$ may be as follows.

R may be an aliphatic acyl group having 2 to 9 carbon atoms, preferably 2 to 4 carbon atoms.

When $R^1$ is a lower alkyl group, the number of carbon atoms of the lower alkyl group may be from 1 to 5, preferably from 1 to 2.

When $R^2$ is an aliphatic acyl group, the number of carbon atoms of the aliphatic acyl group may be from 2 to 9, preferably from 2 to 4. When $R^2$ is an aromatic acyl group, an aromatic group in the aromatic acyl group may be a phenyl or naphthyl group which is optionally substituted with an alkyl group and the like, and the number of carbon atoms of the aromatic acyl group may be from 7 to 12 (in case of the phenyl group), or from 11 to 19 (in case of the naphthyl group).

$R^3$ may be a chlorine atom, a bromine atom, a fluorine atom or a iodine atom.

When $R^4$ is a thioacyl group, the acyl group may be an aliphatic or aromatic acyl group. When $R^4$ is an aliphatic acyl group, the number of carbon atoms of the aliphatic acyl group may be from 2 to 9, preferably from 2 to 4. When $R^2$ is an aromatic acyl group, an aromatic group in the aromatic acyl group may be a phenyl or naphthyl group which is optionally substituted with an alkyl group and the like, and the number of carbon atoms of the aromatic acyl group may be 7 to 12 (in case of the phenyl group), or 11 to 19 (in case of the naphthyl group).

When $R^4$ is a thioalkyl group, the number of carbon atoms of the alkyl group may be from 1 to 8, preferably from 1 to 4.

When $R^4$ is a thioaryl group, an aromatic group may be a phenyl or naphthyl group which is optionally substituted with an alkyl group and the like, and the number of carbon atoms of the thioaryl group may be from 6 to 11 (in case of the phenyl group), or from 10 to 18 (in case of the naphthyl group).

The compounds (I), (II), (III) and (IV) correspond to those obtained by fluorinating the hydroxyl group at the 7-position of 2,3-didehydrosialic acid. These compounds are not disclosed in literatures.

The 2,3-didehydrosialic acid derivative is an important compound which exhibits a sialidase inhibition activity. It is useful to synthesize a derivative modified chemically with fluorine in order to examine the influence of the chemical structure on the manifestation of its activity. In addition, this fluorine-substituted 2,3-didehydrosialic acid can be used for developing practical medicines and for clinical applications.

Accordingly, the development of the synthetic route of the above-described 2,3-didehydrosialic acid of the present invention and the provision in the practical amount are extremely significant.

Thus, the present inventors have produced this fluorine-substituted 2,3-didehydrosialic acid as the objective compound by firstly synthesizing a chloro-acyl derivative of fluorine-containing sialic acid, treating it with an organic base to give a 2,3-didehydro derivative and subjecting the derivative to a hydrolysis reaction process.

It can be also produced by substituting chlorine of the chloro-acyl derivative with SMe, converting into a 2,3-didehydro derivative and subjecting the derivative to a hydrolysis reaction process.

Firstly, the chloro-acetyl derivative of the fluorine-containing sialic acid represented by the general formula (II) is produced as the compound (2) according to the reaction process shown in the Reaction Scheme 1. In the reaction process of this Reaction Scheme 1, the compound (2) is obtained by treating the starting material of methyl [5-acetamido-3,5,7-trideoxy-7-fluoro-D-glycero-α-D-galacto-2-nonuropyranosido]nate (compound (1)) with acetyl chloride, followed by concentrating under the reduced pressure. The amount of acetyl chloride may be from 10 to 500 mol, based on 1 mol of the compound (1). For example, the reaction may be carried out at 30° to 40° C. for 1 to 50 hours.

Reaction Scheme 1

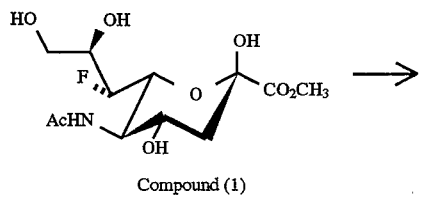

Compound (1)

-continued
Reaction Scheme 1

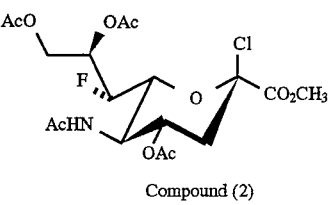

Compound (2)

The SMe sialic acid derivative represented by the general formula (III) is produced as the compound (4) according to the reaction process shown in the Reaction Scheme 2. The compound (3) in which the 2-position of the compound (2) is subjected to SAc-substitution is obtained. The SAc-substitution can be carried out by using a SAc-group forming agent, e.g. potassium thioacetate. The amount of the SAc-group forming agent may be from 2 to 10 mol, based on 1 mol of the compound (2). The reaction may be carried out in a solvent. Examples of the solvent include dichloromethane, chloroform, diethyl ether, dichloroethane, etc. The reaction may be carried out at 0° to 40° C. for 3 to 24 hours.

Then, the compound (4) is obtained by reacting the compound (3) with an alkaline metal alkoxide at a low temperature in a solvent of alcohol, evaporating the solvent, reacting with methyl iodide at a room temperature or a slightly elevated temperature in a suitable aprotic solvent such as dimethylformamide, and then treating according to a conventional method. Examples of an alkaline metal in the alkaline metal alkoxide include lithium, sodium, potassium, etc. The amount of the alkaline metal alkoxide may be from 0.5 to 1 mol, based on 1 mol of the compound (3). The reaction may be carried out at the temperature of −60° to −15° C. for 1 to 30 minutes.

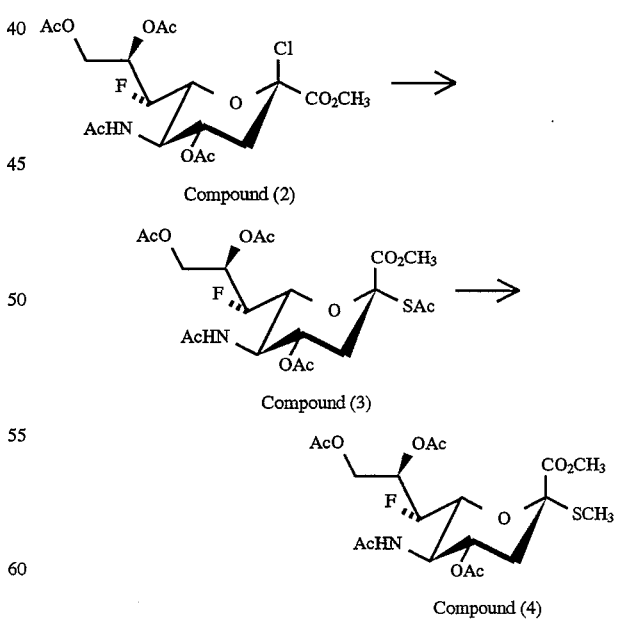

As shown in the Reaction Scheme 3, a 2,3-didehydrosialic acid derivative (compound (5)) represented by the general formula (I) can be obtained by treating the compound (2) or (4) with 1,8-diazabicyclo[5.4.0]undec-7-ene (DBU) or using N-iodosuccinimide and a catalytic amount of trifluoromethanesulfonic acid.

The amount of DBU may be from 1 to 5 mol, based on 1 mol of the compound (2). For example, the reaction with DBU may be carried out at −10° to 40° C. for 0.5 to 4 hours. This reaction may be carried out in a solvent. Examples of the solvent include methylene chloride, diethyl ether, benzene, etc.

The amount of N-iodosuccinimide may be from 1 to 6 mol, based on 1 mol of the compound (4). The amount of trifluoromethanesulfonic acid may be from 0.1 to 1 mol, based on 1 mol of the compound (4). The reaction may be carried out at −40° to 20° C. for 1 to 6 hours. This reaction may be carried out in a solvent. Examples of the solvent include propionitrile, acetonitrile, dimethylformamide, methylene chloride, etc.

Reaction Scheme 3

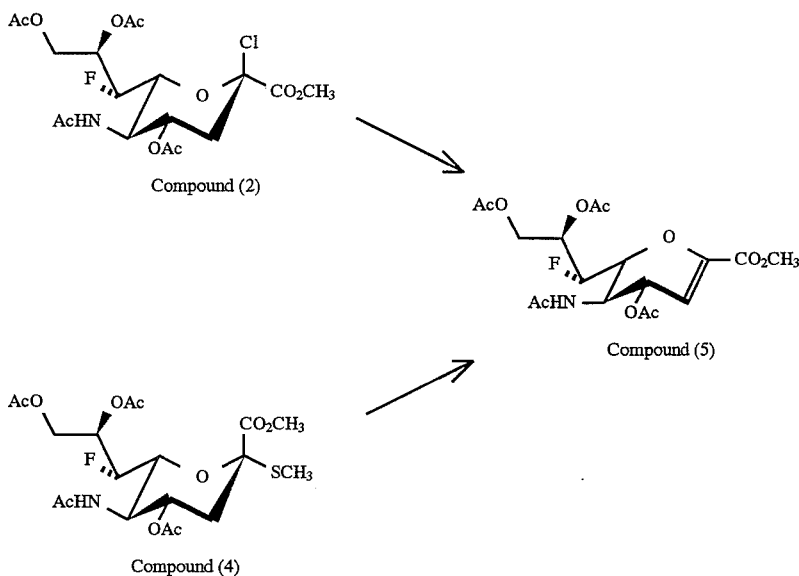

-continued
Reaction Scheme 4

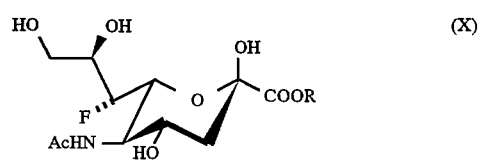

(IV)

A desired fluorine-substituted 2,3-didehydrosialic acid derivative (IV) is obtained by removing a protecting group of the compound (5) prepared as described above. The removal can be carried out by treating with sodium methoxide in methanol and adding an aqueous solution of sodium hydroxide. The amount of a removing agent may be from 0.02 to 100 mol, based on 1 mol of the compound (5). For example, the reaction may be carried out at −10° to 40° C. for 0.5 to 6 hours. This reaction process is as shown in Reaction Scheme 4.

Reaction Scheme 4

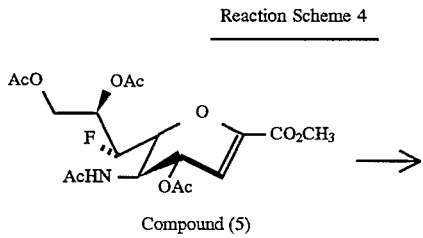

Compound (5)

Further, 7-deoxy-7-fluoro-sialic acid (X):

(X)

wherein R is a hydrogen atom or an alkyl group having 1 to 20 carbon atoms; and Ac is an acetyl group which is used as the starting material for synthesizing the compounds represented by the general formulas (I), (II), (III) and (IV) can be produced as follows.

The compound (X) in which R is the hydrogen atom is N-acetyl-7-deoxy-7-fluoro-neuraminic acid, which is obtained by substituting the hydroxyl group at the 7-position of N-acetyl-neuraminic acid with a fluorine atom. In order to introduce the fluorine atom at the 7-position while maintaining the configuration of N-acetyl-neuraminic acid, there can be used the method comprising protecting the hydroxyl groups, other than the hydroxyl group at the 7-position, with a suitable protecting group, subjecting these hydroxyl groups to Walden inversion, followed by fluorinating with a corresponding fluorinating reagent. However, the 7-position of N-acetyl-neuraminic acid is adjacent to a pyranose ring and, therefore, the side reaction is liable to proceed at Walden inversion and fluorinating reaction because of a steric hindrance.

In order to avoid these difficulties, an aldol condensation between N-acetyl-4-deoxy-4-fluoro-D-glucosamine and sodium pyruvate is carried out using N-acetyl-neuraminic acid aldolase in the present invention. This reaction is shown by the following Reaction Scheme, thereby producing the compound (X) in which R is hydrogen [i.e. compound (X-1)].

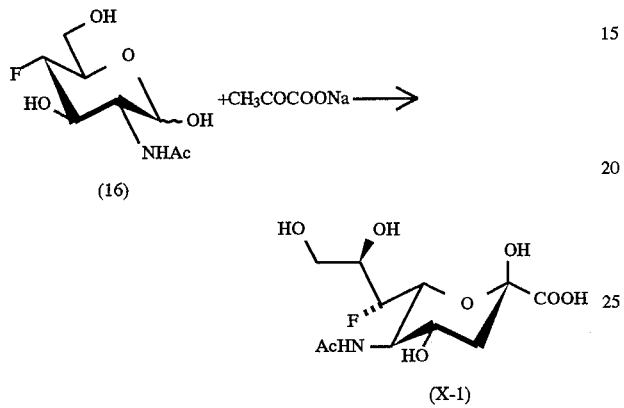

N-acetyl-4-deoxy-4-fluoro-D-glucosamine as the raw material is synthesized from N-acetyl-glucosamine [M. Sharma et at., Carbohydr. Res., Vol. 198 (1990), 202–221]. In this process, there can also be used a method of selectively subjecting the starting material of commercially available N-acetyl-D-galactosamine to inversion/fluorinating at 4-position. Thereby, the two processes can be shorten.

For example, the compound (X) can be obtained according to the following reaction scheme.

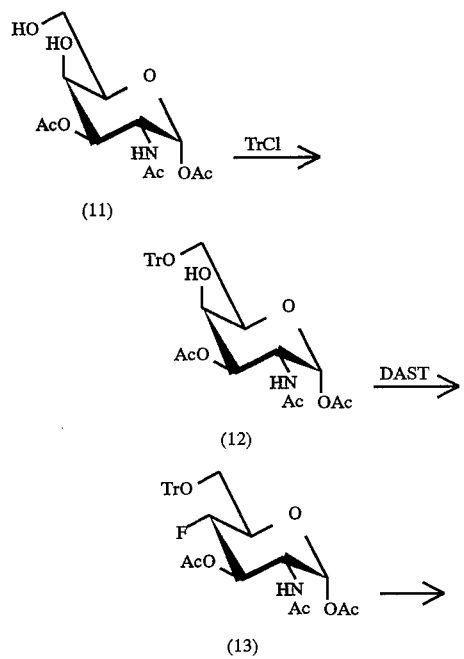

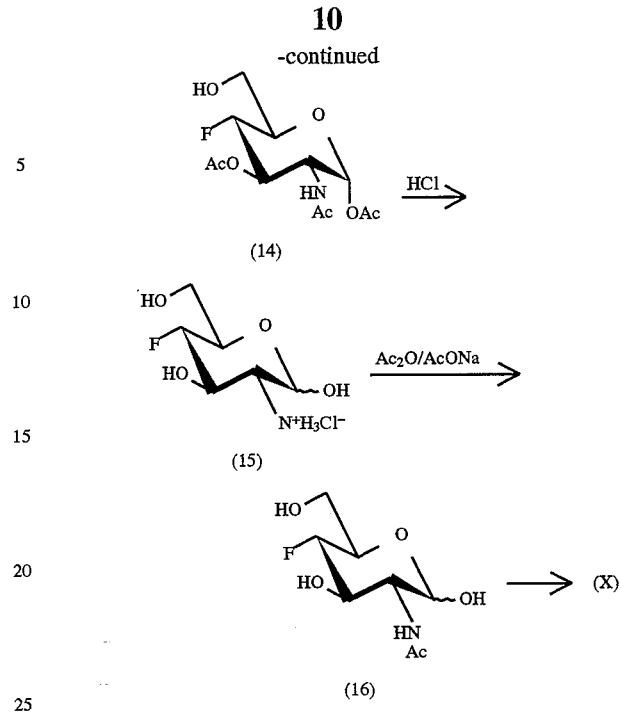

[wherein Tr is $(C_6H_5)_3C$—].

1,3-Di-O-acetyl-N-acetyl-α-D-galactosamine (11) is synthesized by the method of H. G. Flecher et al. [Carbohydr. Res., Vol. 29, (1973), 209–222] and it is tritylated with trityl chloride in a solvent to give crystalline 1,3-di-O-acetyl-N-acetyl-6-O-trityl-α-D-galactosamine (12).

The solvent to be used for the tritylation may be various organic solvents, for example, a heterocyclic aromatic compound (e.g. pyridine, etc.). The amount of the solvent may be 800 to 1500 parts by weight, based on 100 parts by weight of the compound (11). The reaction temperature for the tritylation may be normally from 0° to 50° C., preferably from 15° to 30° C. The reaction time for the tritylation may be normally from 0.5 to 72 hours, preferably from 2 to 24 hours.

The compound (12) is fluorinated with a fluorinating agent to obtain 1,3-di-O-acetyl-2-acetamide-2,4-dideoxy-4-fluoro-6-O-trityl-α-D-glucopyranose (13) as a crystal.

The fluorinating agent may be, for example, diethylamino sulfur trifluoride (DAST), sulfur tetrafluoride, etc. In the reaction, an organic solvent may be used. Examples of the organic solvent include an alkyl halide (e.g. methylene chloride, etc.), diglyme, toluene, benzene, etc. The amount of the solvent may be from 500 to 1500 parts by weight, based on 100 parts by weight of the compound (12). The reaction temperature may be normally from –40° to 35° C., preferably from –30° to 20° C. The reaction time may be normally from 0.5 to 5 hours, preferably from 1 to 2 hours.

1,3-Di-O-acetyl-2-acetamido-2,4-dideoxy-4-fluoro-D-glucopyranose (14) can be obtained by detritylating 1,3-di-O-acetyl-2-acetamido-2,4-dideoxy-4-fluoro-6-O-trityl-α-D-glucopyranose (13).

The detritylation can be carried out by using an aqueous solution of an acid (e.g. acetic acid, trifluoroacetic acid, etc.) as a solvent. The content of acetic acid in an aqueous acetic acid solution to be used as the solvent may be preferably from 70 to 95% by weight. The amount of the solvent may be from 2000 to 4000 parts by weight, based on 100 parts by weight of the compound (13). The reaction temperature may be normally from 10° to 70° C., preferably from 20° to 55° C. The reaction time may be normally from 1 to 5 hours, preferably from 2 to 3 hours.

4-Deoxy-4-fluoro-D-glucosamine hydrochloride (15) can be obtained as a crystal by hydrolyzing 1,3-di-O-acetyl-2-acetamido-2,4-dideoxy-4-fluoro-D-glucopyranose (14) in hydrochloric acid.

The concentration of hydrochloric acid to be used may be from 1 to 5N. The amount of hydrochloric acid may be from 1,000 to 2,500 parts by weight, based on 100 parts by weight of the compound (14). The reaction temperature may be normally from 50° to 100° C., preferably from 70° to 90° C. The reaction time may be normally from 1 to 8 hours, preferably from 2 to 5 hours.

N-acetyl-4-deoxy-4-fluoro-D-glucosamine (16) can be obtained as a crystal by reacting 4-deoxy-4-fluoro-D-glucosamine hydrochloride (15) with acetic anhydride in an organic solvent in the presence of sodium acetate.

The organic solvent may be alcohols (e.g. methanol, ethanol, etc.). The amount of sodium acetate may be from 25 to 50 parts by weight, based on 100 parts by weight of the compound (15). The amount of acetic anhydride may be from 150 to 300 parts by weight, based on 100 parts by weight of the compound (15). The reaction temperature may be normally from −10° to 50° C., preferably from 0° to 25° C. The reaction time may be normally from 1 to 10 hours, preferably from 2 to 6 hours.

The compound (X) in which R is hydrogen [N-acetyl-7-deoxy-7-fluoro-neuraminic acid] can be obtained by reacting N-acetyl-4-deoxy-4-fluoro-D-glucosamine (16) with sodium pyruvate in water in the presence of N-acetyl-neuraminic acid aldolase.

The amount of sodium pyruvate may be normally from 50 to 200 parts by weight, preferably from 80 to 120 parts by weight, particularly 100 parts by weight, based on 100 parts by weight of the compound (16). The amount of water may be from 1 to 50 ml, preferably from 2 to 35 ml, particularly 3.5 ml, based on 1 g of the compound (16). The pH of the aqueous solution is preferably adjusted to 9.5 to 12, more preferably 10 to 11, particularly 10.59. High pH is not preferred because pyruvic acid as the secondary raw material becomes into a polymer. There can be used alkali (e.g. sodium hydroxide, potassium hydroxide, calcium hydroxide, etc.) for the adjustment of the pH. Further, a buffer solution is not particularly required. Examples of N-acetyl-neuraminic acid aldolase include 4.1.3.3. derived from a microorganism. The amount of N-acetyl-neuraminic acid aldolase may be normally from 1 to 500 units, preferably from 5 to 200 units, based on 1 g of the compound (16). The reaction temperature in the enzyme reaction may be normally from 15° to 45° C., preferably from 20° to 35° C. The reaction time may be normally from 1 to 7 days, preferably from 2 to 5 days. It is preferred to treat the reaction product obtained by the enzyme reaction with an ion exchange resin. It is preferred to elute with an aqueous formic acid solution by using a HCOOH-type ion exchange resin after desalting with a H-type ion exchange resin.

N-acetyl-7-deoxy-7-fluoro-neuraminic acid alkyl ester [i.e. compound (X) in which R is an alkyl group] can be obtained by esterifying the compound (X) in which R is hydrogen in a $C_1$–$C_{20}$ alkyl alcohol.

The $C_1$–$C_{20}$ alkyl alcohol is a monohydric alcohol. In addition, it is preferred to use an anhyhdrous alkyl alcohol. It is preferred that the number of carbon atoms of the alkyl group is from 1 to 4. The amount of the alkyl alcohol is from 500 to 20,000 parts by weight, preferably from 2,000 to 10,000 parts by weight, based on 100 parts by weight of the compound (X).

The compound (X) in which R is a methyl group is the above-described compound (1).

4-Deoxy-4-fluoro-D-glucosamine hydrochloride is important as an intermediate of a N-acetyl-glucosamine analogue.

The compounds of the formulas (I) to (IV) and (X) are useful compounds which can be used as drugs such as a carcinostatic agent, a metastasis inhibitor, an antiviral agent, a platelet aggregation inhibitor, an immunomodulation agent, etc., and which can be used as intermediates of examination reagents as well as biochemical reagents after their raw materials and affinities are adjusted.

The compounds of the formulas (I) to (IV) and (X) can be used as drugs (e.g. a carcinostatic agent or metastasis inhibitor due to changing the amount of N-acetyl-neuraminic acid of the membrane surface of tumor cells, an antiviral agent against influenza and AIDS, a platelet aggregation inhibitor due to competition action to phospholipid metabolic enzyme, an immunomodulation agent due to N-acetyl-neuraminic acid metabolic system of lymphocytes, etc.), intermediates of examination reagents and biochemical reagents.

It is extremely difficult to introduce fluorine at the 7-position of natural sialic acid. Namely, the 7-position locates at the first position of a carbon chain extending from a pyranose structure of sialic acid, which results in steric hindrance due to the pyranose structure and protecting groups of hydroxyl groups at the 8- and 9-positions. Therefore, it is difficult to react with a reagent. In addition, it is further difficult to introduce a fluorine atom while maintaining the configuration of the 7-position.

The present inventors have accomplished to synthesize the objective 2,7-dideoxy-7-fluoro-2,3-didehydrosialic acid by stereoselectively substituting the 7-position of sialic acid with the fluorine atom.

EXAMPLES

The following Examples further illustrate the present invention in detail, but these do not limit the scope of the present invention.

Synthesis Example 1

Synthesis of 1,3-di-O-acetyl-N-acetyl-6-O-trityl-α-D-galactosamine (12)

1,3-Di-O-acetyl-N-acetyl-α-D-galactosamine (11) (7.938 g) was dissolved in anhydrous pyridine (90 ml), to which was added trityl chloride (11.025 g), and the mixture was stirred at room temperature for 24 hours. After the completion of the reaction, the reaction solution was poured into ice water, extracted with chloroform, dried over anhydrous sodium sulfate, concentrated, dissolved in toluene and allowed to stand to give 11.138 g of the titled compound (12) as a crystal. The mother solution was concentrated and dissolved in ethanol to give a crystal of triphenylcarbinol, which was filtered. The ethanol filtrate was concentrated again, dissolved in toluene and allowed to stand to give 1.441 g of a secondary crop of the title compound (12) (yield: 79.6%).

Melting point: 177.1°–178.0° C.

$[\alpha]_D$: +80.3° (c=1.00, CHCl$_3$)

NMR (CDCl$_3$; 200 MHz) δ (ppm): 1.95 (s, 3H, NAc), 2.15 (s, 6H, OAcx2), 2.89 (d, 1H, $J_{4, OH}$=2.7 Hz, OH), 3.32 (dd, 1H, $J_{5,6a}$=4.5 Hz, $J_{6a,6b}$=10.0 Hz, H-6a), 3.53 (dd, 1H, $J_{5,6a}$=6.1 Hz, $J_{6a,6b}$=10.0 Hz, H-6b), 3.85 (m, 1H, H-5), 4.18 (m, 1H, H-4), 4.85 (ddd, 1H, H-2), 5.15 (dd, 1H, $J_{3,4}$=3.0 Hz, $J_{2,3}$=11.2 Hz, H-3), 5.48 (d, 1H, $J_{2,NH}$=9.2 Hz, N–H), 6.22 (d, 1H, $J_{1,2}$=3.7 Hz, H-1), 7.48–7.25 (m,15H, Phx3).

Synthesis Example 2

Synthesis of 1,3-di-O-acetyl-2-acetamido-2,4-dideoxy-4-fluoro-6-O-trityl-α-D-glucopyranose (13)

1,3-Di-O-acetyl-N-acetyl-6-O-trityl-α-D-galactosamine (12) (10.212 g) was dissolved in anhydrous methylene chloride (87 ml). This solution was cooled to −31° C. and DAST (6.1 ml) was added dropwise over 5 minutes. Thereafter, the mixture was stirred at −28° to −17° C. for 30 minutes and then at room temperature for 15 minutes. The reaction solution was poured into an aqueous solution of 5% sodium bicarbonate on which ice is floating, extracted with methylene chloride, dried over anhydrous sodium sulfate and then concentrated. The residue was dissolved in ethyl acetate and allowed to stand to give a white crystal. The mother solution was concentrated and dissolved in ether to give a secondary crop.

Yield: 6.705 g, 65.4%.
Melting point: 201°–203.5° C.
$[\alpha]_D$: +69.8° (c=0.25, chloroform)
H-NMR (CDCl$_3$; 500 MHz) δ (ppm): 1.95 (s, 3H, NAc), 2.13 (s, 3H, OAc), 2.16 (s, 3H, OAc), 3.26 (ddd, 1H, $J_{5,6a}$=3.8 Hz, $J_{6a,6b}$=10.6 Hz, $J_{F,6a}$=1.8 Hz, H-6a), 3.41 (ddd, 1H, $J_{5,6b}$=2.0 Hz, $J_{6a,6b}$=10.6 Hz, $J_{F,6b}$=2.0 Hz, H-6b), 3.89 (m, 1H, H-5), 4.46 (m, 1H, H-2), 4.84 (ddd, 1H, $J_{3,4}$=$J_{4,5}$=9.5 Hz, $J_{F,4}$=50.3 Hz, H-4), 5.30 (ddd, 1H, $J_{3,4}$=9.0 Hz, $J_{2,3}$=11.5 Hz, $J_{F,3}$=13.8 Hz, H-3), 5.61 (d, 1H, $J_{2,NH}$=8.9 Hz, N-H), 6.24 (dd, 1H, $J_{1,2}$=$J_{F,1}$=3.2 Hz, H-1), 7.47–7.23 (m, 15H, Phx3).
F-NMR (CDCl$_3$; 470 MHz, CFCl$_3$ standard) 197.70 ppm (dd, $J_{F,H}$=50.3 Hz, $J_{F,3}$=13.6 Hz).

Synthesis Example 3

Synthesis of 1,3-di-O-acetyl-2-acetamido-2,4-dideoxy-4-fluoro-D-glucopyranose (14)

The compound (13) (10.864 g) was dissolved in an aqueous 90% acetic acid (330 ml) and the solution was stirred at 50° C. for 3 hours. After the completion of the reaction, the solution was concentrated. The residue was dissolved in ethanol to deposit triphenylcarbinol, and the mixture was filtered and concentrated again to obtain a syrup. The syrup was purified by a column chromatography [chloroform/methanol (100:1)] using Wako gel C-200 to give 5.150 g of the compound (14) (yield: 91.5%).

$[\alpha]_D$: +66.7° (c=1.02, CHCl$_3$)
H-NMR (CDCl$_3$; 500 MHz) δ (ppm): 1.95 (s, 3H, NAc), 2.14 (s, 3H, OAc), 2.19 (s, 3H, OAc), 3.76–3.80 (m, 1H, H-5), 3.84–3.90 (m, 2H, H-6a, H-6b), 4.37 (dd, dd, 1H, $J_{1,2}$=3.3 Hz, $J_{2,3}$=11.1 Hz, $J_{2,NH}$=8.7 Hz, $J_{F,2}$=1.0 Hz, H-2), 4.67 (ddd, 1H, $J_{3,4}$=$J_{4,5}$=9.4 Hz, $J_{F,4}$=50.5 Hz, H-4), 5.35 (ddd, 1H, $J_{3,4}$=9.0 Hz, $J_{2,3}$=11.1 Hz, $J_{F,3}$=14.0 Hz, H-3), 5.70 (d, 1H, $J_{2,NH}$=8.7 Hz, N-H), 6.15 (dd, 1H, $J_{1,2}$=14.0 Hz, H-3), 5.70 (d, 1H, $J_{2,NH}$=8.7 Hz. N-H), 6.15 (dd, 1H, $J_{1,2}$=$J_{F,1}$=3.3 Hz, H-1).
F-NMR (CDCl$_3$; 470 MHz, CFCl$_3$ standard) 197.96 ppm (m, $J_{F,H}$=50.5 Hz, $J_{F,3}$=14.0 Hz).

Synthesis Example 4

Synthesis of 4-deoxy-4-D-glucosamine hydrochloride (15)

The compound (14) (5.100 g) was reacted in a 3N hydrochloric acid (85 ml) at 90° C. for 3 hours. After the reaction product was decolored with an active carbon and concentrated, water was added and the residual hydrochloric acid was removed by subjecting to azeotropic distillation twice. The mixture was dissolved in methanol and then ether was added to give 2.471 g of the title compound (15) as a needle crystal (yield: 68.4%).

Decomposition point: 162° C.
$[\alpha]_D$: +92.6° (c=0.90, methanol)
H-NMR (CD$_3$OD; 500 MHz) δ (ppm): 3.12 (dd, 1H, $J_{1,2}$=3.2 Hz, $J_{2,3}$=10.5 Hz, H-2), 3.74 (ddd, 1H, $J_{5,6a}$=4.1 Hz, $J_{F,6a}$=1.7 Hz, $J_{6a,6b}$=12.2 Hz, H-6a), 3.78 (ddd, 1H, $J_{5,6b}$=$J_{F,6b}$=2.2 Hz, $J_{6a,6b}$=12.2 Hz, H-6b), 3.97 (dddd, 1H, $J_{5,6a}$=2.3 Hz, $J_{5,6b}$=4.1 Hz, H-5), 4.09 (ddd, 1H, $J_{3,4}$=8.6 Hz, $J_{2,3}$=10.5 Hz, $J_{F,3}$=19.2 Hz, H-3), 4.33 (ddd, 1H, $J_{3,4}$=8.7 Hz, $J_{4,5}$=9.8 Hz, $J_{F,4}$=50.7 Hz, H-4), 5.33(dd, 1H, $J_{1,2}$=$J_{F,1}$=3.3 Hz, H-1).
F-NMR (CD$_3$OD; 470 MHz, CF$_3$COOH standard) 123.07 ppm (m, $J_{F,H}$=50.3 Hz).

Synthesis Example 5

Synthesis of N-acetyl-4-deoxy-4-fluoro-D-glucosamine (16)

Hydrochloride (15) (3.476 g) was dissolved in anhydrous methanol (70 ml) at a room temperature, sodium acetate anhydride (1.310 g) was added and the mixture was stirred for 30 minutes. The resulting solution was ice-cooled and acetic acid anhydride (6 ml) was added dropwise. After the addition, the temperature was returned to the room temperature, followed by stirring for 3.5 hours. After the completion of the reaction, the reaction solution was concentrated and subjected to the azeotropic concentration using methanol-benzene until the odor of acetic acid disappeared. The resultant was dissolved in ethanol to deposit a white insoluble material which was filtered off. The resulting filtrate was concentrated and dissolved in ethanol again, and then the ether was added to give 1.887 g of the title compound (16) as a crystal (yield: 53.0%).

Melting point: 180.1°–180.5° C.
$[\alpha]_D$: +61.4° (c=0.96, methanol)
H-NMR (CD$_3$OD; 500 MHz) δ (ppm): 1.99 (s, 3H, N-COCH$_3$), 4.26 (ddd, 1H, $J_{3,4}$=8.6 Hz, $J_{4,5}$=9.7 Hz, $J_{F,4}$=50.9 Hz, H-4β), 4.30 (ddd, 1H, $J_{3,4}$=8.5 Hz, $J_{4,5}$=9.8 Hz, $J_{F,4}$=51.0 Hz, H-4α), 4.65 (d, 1H, $J_{1,2}$=8.4 Hz, H-1β), 5.09 (dd, 1H, $J_{1,2}$=$J_{F,1}$=3.3Hz, H-1α).
F-NMR (CD3OD; 470 MHz, CFCl$_3$ standard) 196.84 (m, $J_{F,H}$=51.2 Hz, $J_{F,3}$=15.5 Hz, Fα), 198.89 (m, $J_{F,H}$=50.8 Hz, $J_{F,3}$=16.0, Fβ) ppm.

Synthesis Example 6

Synthesis of N-acetyl-7-deoxy-7-fluoro-neuraminic acid [compound (X) in which R is hydrogen]

The compound (16) (1.241 g), sodium pyruvate (1.200 g) and sodium azide (4.3 mg) were dissolved in distilled water (4.3 ml) and the pH of the resulting solution was adjusted to 10.59 by 2N sodium hydroxide. To this solution, 4.3 mg (112 U) of N-acetyl-neuraminic acid aldolase (NAL-300, manufactured by Toyobo Co., Ltd.) was added, followed by stirring mildly at 20° C. for 4 days. Thereafter, the reaction solution was desalted with an ion exchange resin (Dowex 50X8-200, H-type) and purified by an ion exchange chromatography (Dowex 1, HCOOH-type; aqueous 1.0M-HCOOH solution) to give 0.342 g of the candy-like titled compound (yield: 19.2%).

$[\alpha]_D$: −33.2° (c=0.64, H$_2$O)
H-NMR (D$_2$O; 500 MHz, TSP) δ (ppm): 1.93 (dd, 1H, $J_{3a,3e}$=13.1 Hz, $J_{3a,4}$=11.4 Hz, H-3a), 2.07 (s, 3H, N-Ac), 2.35 (dd, 1H, $J_{3a,3e}$=13.1 Hz, $J_{3e,4}$=5.0 Hz, H-3e), 3.69 (ddd, 1H, $J_{9a,9b}$=12.2 Hz, $J_{8,9b}$=5.3 Hz, $J_{F,9b}$=2.3 Hz, H-9b), 3.82 (ddd, 1H, $J_{9a,9b}$=12.2 Hz, $J_{8,9a}$=$J_{F,9a}$=2.9 Hz, H-9a), 3.95 (dd, 1H, $J_{4,5}$=$J_{5,6}$=10.5 Hz, H-5), 3.98 (ddd, 1H, $J_{8,9a}$=2.9 Hz, $J_{8,9b}$=5.3 Hz, $J_{7,8}$~0 Hz, H-8) 4.08 (ddd, 1H, H-4), 4.12

(ddd, 1H, $J_{5,6}$=10.7 Hz, $J_{6,7}$=0.6 Hz, $J_{F,6}$=29.3 Hz, H-6), 4.53 (ddd, 1H, $J_{6,7}$=0.6 Hz, $J_{7,8}$=9.8 Hz, $J_{F,7}$=46.0 Hz, H-7). F-NMR (D$_2$O; 470 MHz, CFCl3 standard) 132.58 ppm (m, $J_{F,7}$=46.0 Hz, $J_{F,6}$=30.1 Hz).

Synthesis Example 7

Synthesis of N-acetyl-7-deoxy-7-fluoro-neuraminate methyl ester [the compound (X) in which R is a methyl group, i.e. the compound (1)]

The compound (X) in which R is hydrogen (1.860 g) was dissolved in anhydrous methanol (180 ml), to which was added an ion exchange resin (Dowex 50X8, H-type) (obtained by washing three times with anhydrous methanol and drying overnight in a vacuum desiccator containing diphosphorus pentaoxide and potassium hydroxide) and the mixture was stirred at 25° C. for 2 hours. After the completion of the reaction, the mixture was filtered and the filtrate was concentrated and the residue was purified with a silica gel column (Wako gel C-200) (chloroform:methanol=4:1) to give 0.94 g of the titled compound (yield: 47.8%).
Melting point: 154.3°–155.3° C.
[α]D: −25.8° (C=0.99, methanol)
H-NMR (CD$_3$OD; 500 MHz) δ (ppm): 1.90 (dd, 1H, $J_{3a,3e}$=12.4 Hz, $J_{3a,4}$=11.3 Hz-3a), 1.99 (s, 3H, N-Ac), 2.19 (dd, 1H, $J_{3a,3e}$=12.6 Hz, $J_{3e,4}$=4.8 Hz, H-3e), 3.63 (ddd, 1H, $J_{9a,9b}$=11.7 Hz, $J_{8,9b}$=5.0 Hz, $J_{F,9b}$=2.4 Hz, H-9b), 3.75 (ddd, 1H, $J_{9a,9b}$=11.7 Hz, $J_{8,9a}$=5.0 Hz, $J_{F,9a}$=2.4 Hz, H-9a), 3.78 (s, 3H, OMe), 3.85 (dddd, 1H, $J_{8,9a}$=5.9 Hz, $J_{8,9b}$=5.3 Hz, $J_{7,8}$~0 Hz, H-8), 3.92 (dd, 1H, $J_{4,5}$=$J_{5,6}$=10.2 Hz, H-5), 4.00 (ddd, 1H, $J_{3a,4}$=11.3 Hz, $J_{3e,4}$=4.8 Hz, $J_{4,5}$=10.3 Hz, $J_{4,F}$=0.8 Hz, H-4), 4.12 (ddd, 1H, $J_{5,6}$=10.5 Hz, $J_{6,7}$=0.9 Hz, $J_{F,6}$=29.0 Hz, H-6), 4.42 (ddd, 1H, $J_{6,7}$=0.9 Hz, $J_{7,8}$=9.0 Hz, $J_{F,7}$=46.0, H-7).
F-NMR (CD$_3$OD; 470 MHz, CFCl3 standard) 132.58 ppm (m, $J_{F,7}$=46.0 Hz, $J_{F,6}$=30.1 Hz).

Example 1

Synthesis of methyl (5-acetamide-4,8,9-tri-O-acetyl-2-chloro-3,5,7-trideoxy-7-fluoro-D-glycero-β-D-galacto-2-nonuropyranosido)nate (abbreviated to compound (2))

The compound (1) (1.12 g, 3.44 mmol) was added to acetyl chloride (55 ml) and the mixture was stirred at 36° C. for 16 hours. After the completion of the reaction was confirmed by TLC (chloroform:acetone=7:3), the reaction solution was concentrated under the reduced pressure at 30° C. or less, and then the resulting residue was dissolved in anhydrous benzene and concentrated under the reduced pressure to give 1.60 g of the crude compound (2) (yield: 98.9%).
C$_{18}$H$_{25}$NO$_{10}$ClF (469.86)
[α]$_D$: =−58.7° (c=1.0, CHCl$_3$)
IR$^{KBr}_{max}$cm$^{-1}$: 3700–3150 (NH), 1750 (ester), 1650, 1540 (amide)
$^1$H-NMR (CDCl$_3$; TMS) δ (ppm): 2.07–2.09 (12H, s, 3OAc, NAc), 2.79 (1H, dd, $J_{3e,4}$=4.6 Hz, $J_{3a,3e}$=13.9 Hz, H-3e), 3.87 (3H, s, CO$_2$Me).
$^{19}$F-NMR (CDCl3; CFCl$_3$) δ (ppm): 21.1 (ddd, $J_{F,7H}$=45.7 Hz $J_{F,6H}$=26.1 Hz, $J_{F,8H}$=10.4 Hz, 1F, 7-F).

Example 2

Synthesis of methyl (5-acetamide-4,8,9-tri-O-acetyl-2-S-acetyl-3,5,7-trideoxy-7-fluoro-2-thio-D-glycero-α-galacto-2-nonuropyranosido)nate (abbreviated to compound (3))

The compound (2) (1.60 g, 3.41 mmol) was dissolved in anhydrous dichloromethane (15 ml), potassium thioacetate (1.20 g, 10.5 mmol) was added at an ice temperature, and then the mixture was stirred at a room temperature for 18 hours. After the completion of the reaction was confirmed by TLC (chloroform:ethyl acetate=1:1), the residue concentrated under reduced pressure was dissolved in chloroform (50 ml), washed with a 5% aqueous solution of sodium bicarbonate and water, and then dried over magnesium sulfate. The mixture was filtered and washed with chloroform, and then the filtrate and the washing liquid were combined and concentrated under the reduced pressure. The resulting residue was purified by a flash chromatography [eluent: chloroform:ethyl acetate (1:1)] and then a silica gel chromatography [eluate: chloroform, chloroform/methanol (200:1) and then chloroform/methanol (100:1)] to give 1.19 g of the compound (3) (yield: 68.6%).
C$_{20}$H$_{28}$NO$_{11}$FS (509.52)
$^1$H-NMR (CDCl$_3$: TMS) δ (ppm): 5.46 (d, 1H, $J_{NH,5}$=9.0 Hz, NH), 4.95 (ddd, 1H, $J_{3e,4}$=4.7 Hz, $J_{4,5}$=10.2 Hz, $J_{3a,4}$=10.8 Hz, H-4), 3.79 (3H, s, CO$_2$Me), 2.60 (1H, dd $J_{3e,4}$=4.6 Hz, $J_{3a,3e}$=13.0 Hz, H-3e), 2.28 (s, 3H, SAc), 2.05, 2.06, 2.15 (3s, 9H, 3OA), 1.98 (s, 3H, NAc).
$^{19}$F-NMR (CDCl$_3$; CFl$_3$) δ (ppm): 211 (ddd, $J_{F,7H}$=45.5 Hz, $J_{F,6H}$=26.7 Hz, $J_{F,8H}$=10.9 Hz, 1F, 7-F).

Example 3

Synthesis of methyl (methyl 5-acetamide-4,8,9-tri-O-acetyl-3,5,7-trideoxy7-fluoro-2-thio-D-glycero-α-D-galacto-2-nonuropyranosido)nate (abbreviated to compound (4))

The compound (3) (536 mg, 1.05 mmol) was dissolved in anhydrous methanol (8 ml), and a 0.20N sodium methoxide-methanol solution (5 ml, 1.00 mmol) was added dropwise at −48° C. and the mixture was stirred for 5 minutes. Thereafter, the mixture was concentrated under the reduced pressure with cooling in ice water, dried sufficiently, and dissolved in anhydrous dimethylformamide (3 ml). Then, methyl iodide (0.050 ml, 0.80 mmol) was added, followed by stirring at room temperature for 18 hours. The resulting residue obtained by concentrating under the reduced pressure was purified by a silica gel chromatography [eluent: dichloromethane/methanol (200:1) and then (100:1)] to give 385 mg of the compound (4) (yield: 76.0%).
C$_{19}$H$_{28}$NO$_{10}$FS (481.51)
[α]$_D$: +2.6° (c=0.51, CHCl$_3$)
IR$^{KBr}_{max}$cm$^{-1}$: 3700–3150 (NH), 3150–2800, 1750 (ester), 1650, 1540 (amide)
$^1$H-NMR (CDCl$_3$; TMS) δ (ppm): 5.45 (dddd, 1H, $J_{8,7}$=9.1 Hz, $J_{9,8}$=4.5 Hz, $J_{8,9}$=2.4 Hz, $J_{H,F}$=5.2 Hz, H-8), 5.33 (d, 1H, $J_{NH,5}$=9.2 Hz, NH), 4.95 (ddd, 1H, $J_{3e,4}$=4.7 Hz, $J_{4,5}$=10.2 Hz, $J_{3a,4}$=10.8 Hz, H-4), 4.66 (ddd, 1H, $J_{6,7}$=1.0 Hz, $J_{7,8}$=9.1 Hz, $J_{H,F}$=45.6 Hz, H-7), 4.60 (ddd, 1H, $J_{9',8}$=2.4 Hz, $J_{9,9'}$=12.6 Hz, $J_{H,F}$=2.4 Hz, H-9'), 4.20 (ddd, 1H, $J_{4,5}$=$J_{5,6}$=$J_{5,NH}$=10.2 Hz, H-5), 4.17 (ddd, 1H, $J_{9,8}$=4.5 Hz, $J_{9,9'}$=12.6 Hz, $J_{H,F}$=2.1 Hz, H-9), 3.80 (3H, s, CO$_2$Me), 3.74 (ddd, 1H, $J_{5,6}$=10.7 Hz, $J_{6,7}$=1.0 Hz, $J_{H,F}$=27.2 Hz, H-6), 2.71 (1H, dd, $J_{3e,4}$=4.7 Hz, $J_{3a,3e}$=12.8 Hz, H-3e), 2.06, 2.06, 2.10, 2.15 (4s, 12H, 3OAc, SMe), 1.97 (s, 3H, NAc).
$^{19}$F-NMR (CDCl$_3$; CFCl$_3$) δ (ppm): 211 (ddd, $J_{F,7H}$=45.6 Hz, $J_{F,6H}$=27.2 Hz, $J_{F,8H}$=5.2 Hz, 1F, 7-F).
Mass spectrometric analysis: m/z Calcd. for C$_{19}$H$_{28}$NO$_{10}$FS: 482.150 (M+H);
Found: 482.150.

Example 4

Synthesis of methyl (5-acetamide-4,8,9-tri-O-acetyl-2,6-anhydro-3,5,7-trideoxy-7-fluoro-D-glycero-D-galacto-non-2-enonate) (abbreviated to compound (5))

The compound (2) (200 mg, 0.426 mmol) was dissolved in anhydrous benzene (2 ml), and 1,8-diazabicyclo[5.4.0]undec-7-ene (DBU) (0.14 ml, 0.936 mmol) was added dropwise with stirring. After stirring for 2 hours, the resulting solution was concentrated under the reduced pressure and the residue was purified by a silica gel chromatography [eluent: toluene/acetone (10:1), (8:1), (5:1) and then (3:1)] to give 131 mg of the compound (5) (yield: 71.0%).

$C_{18}H_{24}NO10F$ (433.40)

$[\alpha]_D$: +47.4° (c=1.0, CHCl$_3$)

IR$^{KBr}_{max}$cm$^{-1}$: 3600–3100 (NH), 1730, 1250 (ester), 1670, 1540 (amide), 1150 (ether).

$^1$H-NMR (CDCl$_3$; TMS) δ (ppm): 6.00 (d, 1H, $J_{3,4}$=3.2 Hz, H-3), 5.71 (dd, 1H, $J_{3,4}$=3.2 Hz, $J_{4,5}$=8.2 Hz, H-4), 5.70 (d, 1H, $J_{NH,5}$=8.2 Hz, NH), 5.44 (dddd, 1H, $J_{8,7}$=5.8 Hz, $J_{8,9}$=5.8 Hz, $J_{8,9'}$=3.1 Hz, $J_{H,F}$=12.0 Hz, H-8), 4.83 (ddd, 1H, $J_{7,6}$=3.0 Hz, $J_{8,7}$=5.8 Hz, $J_{H,F}$=46.4 Hz, H-7), 4.68 (ddd, 1H, $J_{8,9}$=3.1 Hz, $J_{9,9'}$=12.4 Hz, $J_{H,F}$=1.6 Hz, H-9'), 4.58 (ddd, 1H, $J_{5,6}$=8.2 Hz, $J_{7,6}$=3.0 Hz, $J_{H,F}$=24.7 Hz, H-6), 4.23 (ddd, 1H, $J_{8,9}$=5.8 Hz, $J_{9,9'}$=12.4 Hz, $J_{H,F}$=1.6 Hz, H-9), 4.19 (ddd, 1H, $J_{5,4}$=$J_{5,6}$=$J_{5,NH}$=8.2 Hz, H-5), 3.80 (s, 3H, CO$_2$Me), 2.07, 2.08, 2.09 (3s, 9H, 3OAc), 2.01 (s, 3H, NAc).

$^{19}$F-NMR (CDCl$_3$; CFCl$_3$) δ (ppm): 210 (ddd, $J_{F,6H}$=24.7 Hz, $J_{F,7H}$=46.4 Hz, $J_{F,8H}$=12.0 Hz, 1F, 7-F).

Example 5

Synthesis of compound (5)

The compound (4) (104 mg, 0.216 mmol) was dissolved in anhydrous propionitrile (2 ml), an activated (dried under vacuum at 180° C. for 6 hours) molecular sieve (4A, 400 mg) was added, and the mixture was stirred overnight under an argon atmosphere. After cooling to −45° C., N-iodosuccinimide (290 mg, 1.29 mmol) and then trifluoromethanesulfonic acid (8 μl 0.091 mmol) were added and the mixture was stirred at −45° to −40° C. for 2 hours. The reaction solution was diluted with chloroform and filtered with Celite, and the insoluble material was washed with chloroform. The filtrate and the washing solution were combined and the organic layer was washed with a 5% aqueous solution of sodium bicarbonate and water. The resultant was dried over anhydrous magnesium sulfate, filtered and washed with chloroform. The filtrate and the washing solution were combined and the resulting residue was purified by a flash chromatography [eluent: ethyl acetate/hexane (3:1)] to give 70 mg of the compound (5) (yield: 74.8%).

$C_{18}H_{24}NO_{10}F$ (433.40)

1-NMR (CDCl$_3$; TMS) δ (ppm): 6.00 (d, 1H, $J_{3,4}$=3.2 Hz, H-3), 5.71 (dd, 1H, $J_{3,4}$=3.2 Hz, $J_{4,5}$=8.2 Hz, H-4), 5.70 (d, 1H, $J_{NH,5}$=8.2 Hz, NH), 5.44 (dddd, 1H, $J_{8,7}$=5.8 Hz, $J_{8,9}$=5.8 Hz, $J_{8,9'}$=3.1 Hz, $J_{H,F}$=12.0 Hz, H-8), 4.83 (ddd, 1H, $J_{7,6}$=3.0 Hz, $J_{8,7}$=5.8 Hz, $J_{H,F}$=46.4 Hz, H-7), 4.68 (ddd, 1H, $J_{8,9}$=3.1 Hz, $J_{9,9'}$=12.4 Hz, $J_{H,F}$=1.6 Hz, H-9'), 4.58 (ddd, 1H, $J_{5,6}$=8.2 Hz, $J_{7,6}$=3.0 Hz, $J_{H,F}$=24.7 Hz, H-6), 4.23 (ddd, 1H, $J_{8,9}$=5.8 Hz, $J_{9,9'}$=12.4 Hz, $J_{H,F}$=1.6 Hz, H-9), 4.19 (ddd, 1H, $J_{5,4}$=$J_{5,6}$=$J_{5,NH}$=8.2 Hz, H-5), 3.80 (s, 3H, CO$_2$Me), 2.07, 2.08, 2.09 (3s, 9H, 3OAc), 2.01 (s, 3H, NAc).

Example 6

Synthesis of 5-acetamide-2,6-anhydro-3,5,7-trideoxy-7-fluoro-D-glycero-D-galacto-non-2-enonic acid (abbreviated to compound (6)) (IV)

The compound (5) (150 mg, 0.346 mmol) was dissolved in anhydrous methanol (23 ml) and a 1M sodium methoxide-methanol solution (10 μl, 0.01 mmol) was added, and the mixture was stirred at a room temperature for 1.5 hours. Then, an aqueous 1N sodium hydroxide solution (23 ml, 23 mmol) was added and the mixture was stirred for one hour. Dowex 50W-X8 (16 g) was added, and the mixture was subjected to a desalting treatment and filtered. The filtrate was concentrated under the reduced pressure to give 99 mg of the compound (6) (yield: 97.3%).

$C_{11}H_{16}NO_7F$ (293.25)

Melting point: 143°–145.5° C.

$[\alpha]_D$: +16.9° (c=1.05, H$_2$O)

IR$^{KBr}_{max}$cm$^{-1}$: 3600–3100 (OH, NH), 1720 (carbonyl), 1660, 1560 (amide), 1150 (ether).

$^1$H-NMR (D$_2$O; DSP) δ (ppm): 6.00 (d, 1H, $J_{3,4}$=2.5 Hz, H-3e), 4.59 (ddd, 1H, $J_{7,6}$=1.1 Hz, $J_{7,8}$=9.3 Hz, $J_{H,F}$=45.4 Hz, H-7), 4.49 (dd, 1H, $J_{4,3}$=2.5 Hz, $J_{4,5}$=8.8 Hz, H-4), 4.31 (ddd, 1H, $J_{6,5}$=10.9 Hz, $J_{6,7}$=1.1 Hz, $J_{H,F}$=28.8 Hz, H-6), 4.16 (m, 1H, H-8), 4.12 (dd, 1H, $J_{5,4}$=8.8 Hz, $J_{5,6}$=10.9 Hz, H-5), 3.85 (ddd, 1H, $J_{9',8}$=$J_{H,F}$=3.0 Hz, $J_{9',9}$=12.2 Hz, H-9'), 3.70 (ddd, 1H, $J_{9,8}$=5.2 Hz, $J_{H,F}$=2.3 Hz, $J_{9,9'}$=12.2 Hz, H-9), 2.06 (s, 3H, NAc).

$^{19}$F-NMR (D$_2$O; CF$_3$CO$_2$H) δ (ppm): 133 (dd, 1F, $J_{F,6H}$=28.8 Hz, $J_{F,7H}$=45.4 Hz, 7-F).

Mass spectrometric analysis: m/z Calcd. for $C_{11}H_{16}NO_7F$: 294.099 (M+H);

Found: 294.099

Effect of the Invention

The compounds of the present invention are useful for developing practical drugs such as an antiviral agent, a preventing agent for viral diseases, etc. and for clinical applications. In addition, they are also useful as a carcinostatic agent and an immunomodulation agent.

We claim:

1. A compound represented by the formula (I):

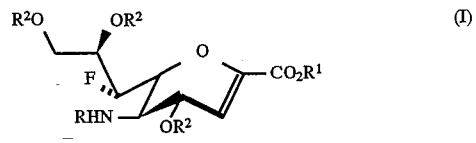

wherein R is an aliphatic acyl group; R$^1$ is a hydrogen atom or a lower alkyl group; each R$^2$ is selected from the group consisting of a hydrogen atom, an aliphatic acyl group and an aromatic acyl group, and each R$^2$ may be the same or different, provided that (i) when R$^1$ is a hydrogen atom then each R$^2$ is a hydrogen atom, and (ii) when R$^1$ is a lower alkyl group then each R$^2$ is the same or different and is selected from the group consisting of an aliphatic acyl group and an aromatic acyl group.

2. A compound represented by the formula (II):

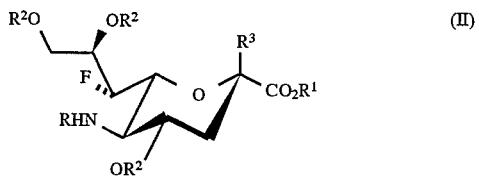 (II)

wherein R is an aliphatic acyl group; $R^1$ is a lower alkyl group; each $R^2$ is selected from the group consisting of an aliphatic acyl group and an aromatic acyl group, wherein each $R^2$ may be the same or different; and $R^3$ is a halogen atom.

3. A compound represented by the formula (III):

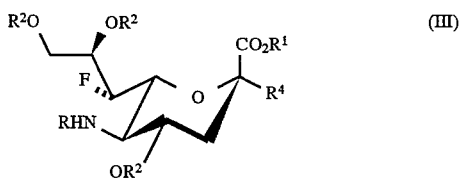 (III)

wherein R is an aliphatic group; $R^1$ is a lower alkyl group; each $R^2$ is selected from the group consisting of a hydrogen atom, an aliphatic acyl group and an aromatic acyl group, wherein each $R^2$ may be the same or different; and $R^4$ is a thioacyl group, a thioalkyl group or a thioaryl group.

4. A 2,3-didehydrosialic acid derivative represented by the formula (IV):

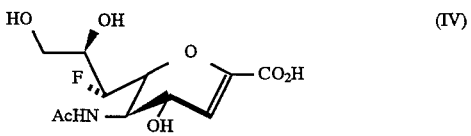 (IV)

wherein Ac is an acetyl group.

5. A N-acetyl-7-deoxy-7-fluoro-neuraminic acid derivative represented by the formula (X):

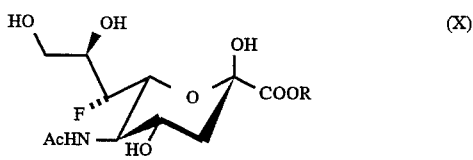 (X)

wherein R is a hydrogen atom or an alkyl group having 1 to 20 carbon atoms; and Ac is an acetyl group.

6. The N-acetyl-7-deoxy-7-fluoro-neuraminic acid derivative of claim 5, wherein R is an alkyl group having 1 to 4 carbon atoms.

7. 1,3-Di-O-acetyl-2-acetamide-2,4-dideoxy-4-fluoro-6-O-trityl-α-D-glucopyranose represented by the formula:

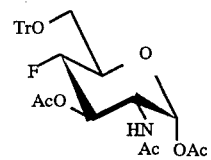

wherein Tr is $(C_6H_5)_3C-$.

8. 4-Deoxy-4-fluoro-D-glucosamine hydrochloride represented by the formula:

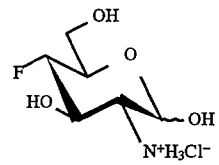

9. A process for producing N-acetyl-7-deoxy-7-fluoro-neuraminic acid, which comprises subjecting N-acetyl-4-deoxy-4-fluoro-D-glucosamine and sodium pyruvate to a condensation reaction in the presence of N-acetyl-neuraminic acid aldolase.

10. A process for producing N-acetyl-7-deoxy-7-fluoro-neuraminic acid alkyl ester, which comprises esterifying N-acetyl-7-deoxy-7-fluoro-neuramic acid by reacting with an alcohol having a $C_1-C_{20}$ alkyl group.

11. A process for producing N-acetyl-4-deoxy-4-fluoro-D-glucosamine, which comprises subjecting 1,3-di-O-acetyl-N-acetyl-D-galactosamine to a tritylation, a fluorination, a detritylation and a hydrolysis with hydrochloric acid, and then subjecting the resulting 4-deoxy-4-fluoro-D-glucosamine hydrochloride to a N-acetylation.

* * * * *